United States Patent [19]
Gage et al.

[11] Patent Number: 6,013,521
[45] Date of Patent: *Jan. 11, 2000

[54] METHOD FOR PRODUCTION OF NEUROBLASTS

[75] Inventors: Fred H. Gage, La Jolla; Jasodhara Ray, San Diego, both of Calif.

[73] Assignee: University of California, Oakland, Calif.

[*] Notice: This patent is subject to a terminal disclaimer.

[21] Appl. No.: 09/065,858

[22] Filed: Apr. 24, 1998

Related U.S. Application Data

[60] Division of application No. 08/147,843, Nov. 3, 1993, Pat. No. 5,766,948, which is a continuation-in-part of application No. 08/001,543, Jan. 6, 1993, abandoned.

[51] Int. Cl.$^7$ ........................................... C12N 5/00
[52] U.S. Cl. .................... 435/368; 435/363; 435/366; 435/384; 435/387; 435/405; 435/406; 435/325; 435/395; 435/402; 536/23.1
[58] Field of Search ........................ 435/368, 366, 435/395, 325, 402, 404, 405, 384, 387, 406; 536/23.1

[56] References Cited

U.S. PATENT DOCUMENTS

| | | | |
|---|---|---|---|
| 5,270,191 | 12/1993 | McKay et al. | 435/172.3 |
| 5,411,883 | 5/1995 | Boss et al. | |
| 5,514,552 | 5/1996 | Rosner et al. | 435/7.21 |
| 5,766,948 | 6/1998 | Gage et al. | 435/368 |

OTHER PUBLICATIONS

Maisonpierre et al., "Neurotrophin–3: A Neurotrophic Factor Related to NGF and BDNF", *Science*, vol. 247, Part I, pp. 1446–1451 (1990).

Saneto et al., "Neuronal and glial cells: cell culture of the central nervous system", *Cell Culture of the CNS,* pp. 27–63, published 1987.

Cattaneo et al.,"Proliferation and differentiation of neuronal stem cells regulated by nerve growth factor", *Nature,* vol. 347, pp. 762–765 (1990).

Walicke et al., "Fibroblast growth factor promotes survival of dissociated hippocampal neurons and enhances neurite extension", *Proc. Natl. Acad. Sci. USA,* vol. 83, pp. 3012–3016 May, 1986.

Piszczkiewicz et al., "Proliferation and Survival of Rat Sensory Neuron Precursors in Vitro", *Soc. For Neuroscience,* Abstract, 19 (Part 2) p. 1709 (1993).

DiCicco et al., "Insulin growth factors regulate the mitotic cycle in cultured rat sympathetic neuroblasts", *Proc. Natl. Acad. Sci. USA,* vol. 85, pp. 4066–4070, Jun. 1988.

Ray et al, "Proliferation, differentiation, and long–term culture of primary hippocampal neurons", *PNAS,* 90(8), pp. 3602–3606 (Apr. 1993).

Gensburger et al., "Brain basic fibroblast growth factor stimulates the proliferation of rat neuronal precursor cells in vitro", Biosis Abstract, FEBS Letter, 217(1) pp. 1–5 (1987).

Pincus et al., "Vasoactive intestinal peptide regulate mitosis, differentiation and survival of cultured symphathetic neuroblasts", *Nature,* vol. 343, pp. 564–567 (1990).

Calof et al., "Identification of a Proliferative Neuronal Precursor Cell in Sultures of a Mammalian . . . , " *J. Cell Biol.,* 107 (6 Part 3) 510A (1988).

Chan et al.,*J. of Cellular Biochemistry,* 45:252–257, 1991.

Lendahl et al., TINS, vol. 13, No. 4, 133–137, 1990.

*Primary Examiner*—F. T. Moezie
*Attorney, Agent, or Firm*—Lisa A. Haile, Ph.D.

[57] ABSTRACT

A method for producing a neuroblast and a cellular composition comprising an enriched population of neuroblast cells is provided. Also disclosed are methods for identifying compositions which affect neuroblasts and for treating a subject with a neuronal disorder, and a culture system for the production and maintenance of neuroblasts.

14 Claims, 5 Drawing Sheets

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Oligonucleotides for PCR

<400> SEQUENCE: 1
gaggagataa ctgagtaccg                                              20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotides for PCR

<400> SEQUENCE: 2
ccaaagccaa tccgacactc                                              20

```
<210> SEQ ID NO 3
<211> LENGTH: 20
<212> TYPE: DNA
<213> ORGANISM: Artificial Sequence
<220> FEATURE:
<223> OTHER INFORMATION: Oligonucleotides for PCR

<400> SEQUENCE: 3
acctcggcac cctgaggcag                                           20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotides for PCR

<400> SEQUENCE: 4
ccagcgactc aaccttcctc                                           20
```

METHOD FOR PRODUCTION OF NEUROBLASTS

This application is a divisional of U.S. patent application Ser. No. 08/147,843, filed Nov. 3, 1993, now U.S. Pat. No. 5,766,948 which is a continuation-in-part of application Ser. No. 08/001,543 filed on Jan. 6, 1993, now abandoned.

BACKGROUND OF THE INVENTION

1. Field of the Invention

This invention relates generally to cell populations derived from neurons, which are denoted neuroblasts, methods for the production and long-term in vitro culture of these cell populations, and the use of neuroblasts in the treatment of various neuronal disorders as well as the identification of compositions which affect neuroblasts.

2. Description of Related Art

Only a few neuronal cell types have been reported to divide in the adult brain and adult neurons do not survive well in vitro. To date, even with all of the recent advances in neurobiology, genetics, immunology and molecular biology, no reliable procedure exists to establish cell lines from the central nervous system (CNS) and neuronal tissues in the absence of immortalization. The generation of clonal cell lines from different regions of the brain is important and will greatly facilitate the discovery of new neurotrophic factors and their receptors, and enhance the understanding of their function.

The central nervous system contains two major classes of cells known as neurons and glial cells. Glial cells include astrocytes, oligodendrocytes and microglia. There are hundreds of different types of neurons and many different neurotrophic factors which influence their growth and differentiation. Depending on the type of neuron and the region of the brain in which the neuron resides, a different neurotrophic factor or specific combination of factors affect the survival, proliferation and differentiation of the neuron. Each type of neuron responds to different combinations of neurotransmitters, neurotrophic factors, and other molecules in its environment.

To date, neuropharmacological studies in the CNS have been delayed by the lack of cell systems needed to investigate potentially useful neuroactive compounds. In live animals, the complexity of the brain makes it difficult to effectively measure which cellular receptors are being targeted by these compounds. Additionally, the expense involved in live animal research and the current controversies stemming from animal rights movements have made in vivo animal studies less acceptable for initial research. Primary cells from neuronal tissue are often used for CNS studies, however, long-term culture of primary neurons has not been achieved. Also, only a few attempts to achieve not only long term culture, but actual proliferation of neuronal cells have been reported. In fact, the proliferation of neuronal cells has proven so elusive that it has become ingrained in the scientific community that neuronal cells do not proliferate in vitro. As a consequence, fresh dissections must be performed for each study in order to obtain the necessary neuronal cell types, resulting in costly research with increased variability in the experimental results.

While some neuronal tumorogenic cells exist they are few in number and are not well characterized. In general, these tumor cell lines do not mimic the biology of the primary neurons from which they were originally established and, as a result, are not suitable for drug discovery screening programs. In vitro primary cultures that would be more phenotypically representative of primary cells and that could generate continuous cultures of specific neuronal cell lines capable of proliferation would be invaluable for neurobiological studies and CNS drug discovery efforts, as well as therapy. It has become increasingly apparent that more defined conditions and further refinements in culture methodology are necessary to produce neuronal cell lines which would enhance the yield of information from in vitro studies of the nervous system. Recognition of cell type and developmental stage-specific requirements for maintaining neural cells in culture as well as the development of a broader range of culture conditions are required. However, in order to achieve these goals it is critical to develop optimal culture methods which mimic in vivo conditions which are devoid of the biological fluids used in conventional culture techniques.

Recently, several researchers have isolated and immortalized progenitor cells from various regions of the brain and different stages of development. Olfactory and cerebellum cells have been immortalized using the viral myc (v-myc) oncogene to generate cell lines with neuronal and glial phenotypes (Ryder, et al., *J.Neurobiology,* 21:356, 1990). Similar studies by Snyder, et al. (*Cell,* 68:33,1992) resulted in multi-potent neuronal cell lines which were engrafted into the rat cerebellum to form neurons and glial cells. In other studies, murine neuroepithelial cells were immortalized with a retrovirus vector containing c-myc and were cultured with growth factors to form differentiated cell types similar to astrocytes and neurons (Barlett, et al., *Proc.Natl.Acad.Sci. USA,* 85:3255, 1988).

Epidermal growth factor (EGF) has been used to induce the in vitro proliferation of a small number of cells isolated from the striatum of the adult mouse brain (Reynolds and Weiss, *Science,* 255:1707 1992). Clusters of these cells had antigenic properties of neuroepithelial stem cells and under appropriate conditions, these cells could be induced to differentiate into astrocytes and neurons with phenotypes characteristic of the adult striatum in vivo. However, it should be noted that these differentiated neurons were not cultured for lengthy periods of time nor was there any evidence that these cells could be frozen and then thawed and recultured.

Cattaneo and McKay (*Nature,* 347:762, 1990) performed experiments using rat striatum to determine the effect of nerve growth factor (NGF) on proliferation of neuronal precursor cells. The cells were dissected from rat embryonic striatum and exposed to both NGF and basic fibroblast growth factor (bFGF, also known as FGF2). These cells were cultured only nine days in vitro, at which time they had differentiated into neurons as determined by assay with neuron-specific markers.

Neuronal precursor cells from the cerebral hemispheres of 13-day old rat embryos have been cultured for up to 8 days in the presence of bFGF at 5 ng/ml (Gensberger, et al., *FEBS Lett.* 217:1, 1987). At this concentration, bFGF stimulated only short-term proliferation. Proliferation and differentiation of primary neurons from both fetal and adult striatum in response to a combination of NGF and bFGF or only EGF have also been reported (Catteneo, et al., supra; Reynolds and Weiss, supra).

In view of the foregoing, there is a need for a long-term in vitro culture system which would allow large scale production and maintenance of a neuronal cell population which will proliferate and can be passaged and subcultured over time. Such homogenous in vitro neuronal cultures will prove invaluable in studying cell populations, the interactions between these cells and the effects of various neuroactive compositions on these cells.

SUMMARY OF THE INVENTION

Recognizing the importance of a system for producing and maintaining neuronal cells in vitro, the inventors developed a method and a culture system for producing continuous fetal and adult neuronal cell lines. The development of primary neuronal cultures maintained as cell lines, known as neuroblasts, using neurotrophic factors in the absence of oncogenic immortalization, now permits investigation of fundamental questions regarding the biochemical and cellular properties of these cells and the dynamics of interaction between their cellular and chemical environment.

The neuroblasts of the invention can advantageously be used to stably incorporate genetic sequences encoding various receptors, ligands and neurotransmitters, for example, for use in the treatment of subjects with neuronal disorders and for identifying compositions which interact with these molecules.

DETAILED DESCRIPTION OF THE INVENTION

Figure 1A:
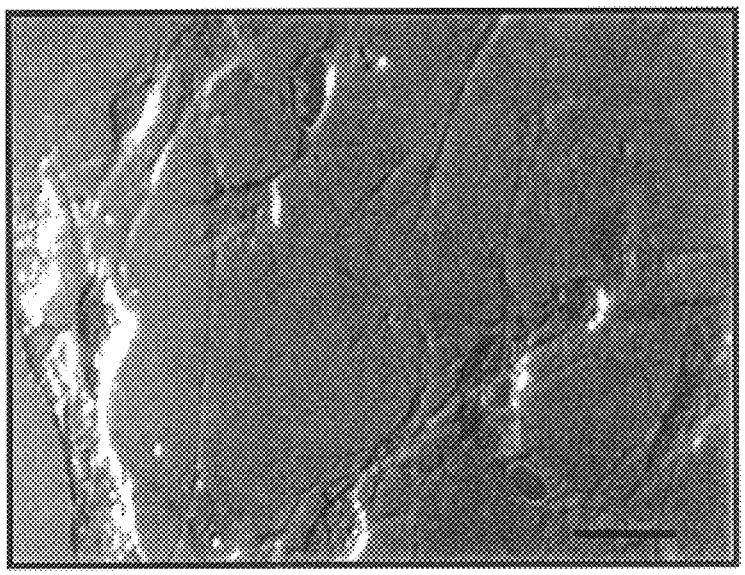
FIG. 1 shows BrdU staining and NeuroTag™ binding of primary neurons in culture. A. Primary neurons were labeled with BrdU for 1 day; and B. for 4 days. C. The neuronal nature of primary cells was determined by binding with tetanus toxin (NeuroTag™). Cell bodies and processes of all cells in culture were stained. Calibration bar=20 $\mu$m.

The present invention provides an in vitro method for producing an isolated neuronal cell population. These cells, termed neuroblasts can be produced by utilizing methodology which comprises culturing a neuronal cell in a serum-free media supplemented with at least one trophic factor using a vessel which allows attachment of the cell. This method allows the generation of continuous, neuronal cell cultures from different regions of the brain, from both fetal and adult tissue, which are capable of proliferation.

The invention also provides a method of identifying compositions which affect a neuroblast, such as by inhibiting or stimulating the neuroblast proliferation. A culture system useful for the production and maintenance of a neuroblast comprising a serum-free basal media containing at least one trophic factor and a vessel which allows attachment of the neuroblast is also provided. An enriched population of neuroblast cells produced by the method of the invention is also provided and can be further utilized for the treatment of a subject with a neuronal cell disorder or alternatively, to screen compositions which affect the neuroblast.

As used herein, the term "neuroblast" refers to a non-glial cell of neuronal lineage which has been perpetualized. Neuronal "perpetualization" refers to the procedure whereby a non-glial cell of the neuronal lineage is treated with growth factors such that it is capable of indefinite maintenance, growth and proliferation in vitro. Typically, a primary culture, one in which the tissue is removed from an animal, is placed in a culture vessel in appropriate fluid medium, and has a finite lifetime. In contrast, continuous cell lines proliferate and thus can be subcultured, i.e., passaged repeatedly into new culture vessels. Continuous cell lines can also be stored for long periods of time in a frozen state in the vapor phase of liquid nitrogen when a cryopreservative is present, e.g., 10% dimethylsulfoxide or glycerol. The neuroblast of the invention can be maintained in long-term culture as a cell line closely resembling primary cultures, but without resort to oncogenic immortalization. Rather, "perpetualization" establishes a continuous culture from a primary neuronal cell by utilizing a specific growth factor or combination of growth factors. This perpetualization technique is novel in that no gene transfer or genetic manipulation is required and, as a consequence, the cells more closely resemble primary cultures.

There are hundreds of different types of neurons, each with distinct properties. Each type of neuron produces and responds to different combinations of neurotransmitters and neurotrophic factors. Neurons do not divide in the adult brain, nor do they generally survive long in vitro. The method of the invention provides for the isolation and growth of perpetualized neurons, or neuroblasts, in vitro, from virtually any region of the brain and spinal cord. Either embryonic or adult neurons can be utilized for the development of neuroblast cell lines. The neuronal cell of the invention, which is utilized for production of a neuroblast, can be derived from any fetal or adult neural tissue, including tissue from the hippocampus, cerebellum, spinal cord, cortex (e.g., motor or somatosensory cortex), striatum, basal forebrain (cholenergic neurons), ventral mesencephalon (cells of the substantia nigra), and the locus ceruleus (neuroadrenaline cells of the central nervous system).

The liquid media for production of a neuroblast of the invention is supplemented with at least one trophic factor to support the growth and proliferation of a neuroblast. Trophic factors are molecules which are involved in the development and survival of neurons. They are often synthesized in the brain, have specific receptors, and influence the survival and function of a subset of neurons. Examples of such factors include nerve growth factor (NGF), brain-derived neurotrophic factor (BDNF), neurotrophin-3, -4, and -5 (NTF-3, -4, -5), ciliary neurotrophic factor (CNTF), basic fibroblast growth factor (bFGF), acidic fibroblast growth factor (aFGF), platelet derived growth factor (PDGF), epidermal growth factor (EGF), insulin-like growth factor-I and -II (GF-I, -II), transforming growth factor (TGF) and lymphocyte infiltrating factor/cholinergic differentiating factor (LIF/CDF). The specificity and selectivity of a trophic factor are determined by its receptor. Preferably, the trophic factor utilized in the invention is a neurotrophic factor. Preferably, the neurotrophic factor added to the basal media for production of a neuroblast according to the method of the invention is bFGF. The neurotrophic factor which allows growth and proliferation of the neuroblast in vitro will depend on the tissue origin of the neuroblast. However, for most neuronal cells, bFGF will be the preferred neurotrophic factor.

The vessel utilized for production of a neuroblast must provide a surface which allows attachment of the neuronal cell. Such vessels are also preferred once the isolated neuroblast culture has been produced. The surface used to enhance attachment of the neuronal cell can be the actual inner layer of the vessel or more indirectly, the surface of a supplemental insert or membrane which resides within the vessel. Attachment may be accomplished by any means which allows the cell to grow as a monolayer on a vessel. Attachment enhancing surfaces can be produced directly, such as by advantageous selecting of appropriate plastic polymers for the vessel or, indirectly, as by treating the surface in the vessel by a secondary chemical treatment. Therefore, "attachment" refers to the ability of a cell to adhere to a surface in a tissue culture vessel, wherein the attachment promoting surface is in direct contact with neuronal cells, which otherwise would grow in a three-dimensional cellular aggregate in suspension. Attachment, or adherence, of a neuronal cell to the vessel surface allows it to be perpetualized.

In addition to interactions with soluble factors, most cells in vivo, including neuronal cells, are in contact with an extracellular matrix, a complex arrangement of interactive protein and polysaccharide molecules which are secreted locally and assemble into an intricate network in the spaces between cells. Therefore, the addition of an extracellular matrix protein to the surface of the culture vessel forms an insoluble matrix which allows neuronal cells in culture to adhere in a manner which closely corresponds to the in vivo extracellular matrix The neuroblast of the invention can be preferably produced by coating the surface of a vessel, such as a tissue culture dish or flask, with a polybasic amino acid composition to allow initial attachment. Such compositions are well known in the art and include polyomithine and polylysine. Most preferably, the polybasic amino acid of the invention is polyomithine. Additionally, the surface of the vessel may be coated with a known extracellular matrix protein composition to enhance the neuroblasts ability to grow and form processes on the substrate. Such compositions include laminin, collagen and fibronectin. Other extracellular matrix proteins that can be used in conjunction with a polybasic amino acid will be apparent to one of skill in the art. Additionally, for the production of adult neuroblasts, it is preferable to initially culture the cells in the presence of serum.

The neuroblast of the invention is useful as a screening tool for neuropharmacological compounds which affect a biological function of the neuroblast. Thus, in another embodiment, the invention provides a method for identifying a composition which affects a neuroblast comprising incubating the components, which include the composition to be tested and the neuroblast, under conditions sufficient to allow the components to interact, then subsequently measuring the effect the composition on the neuroblast. The observed effect on the neuroblast may be either inhibitory or stimulatory. For example, a neuroactive compound which mimics a neurotransmitter or binds to a receptor and exhibits either an antagonistic or agonist effect, thereby inhibiting or stimulating a biological response in the neuroblast, can be identified using the method of the invention. The occurrence of a biological response can be monitored using standard techniques known to those skilled in the art. For example, inhibition or stimulation of a biological response may be identified by the level of expression of certain genes in the neuroblast. Such genes may include early response genes such as fos, myc orjun (Greenberg, M. and Ziff, E. *Nature*, 311:433, 1984; eds. Burck, et al., in *Oncogenes*, 1988, Springer-Verlag, New York.). Other genes, including those which encode cell surface markers can also be used as indicators of the effects neuropharmacological compounds on the neuroblasts of the invention. Methods for measurement of such effects include Northern blot analysis of RNA (transcription), SDS-PAGE analysis of protein (translation), [$^3$H]-thymidine uptake (DNA synthesis) and antibody reactivity (both intracellular and extracellular). Other commonly used methods will be apparent to those of skill in the art.]

Neuroactive drugs which act similarly to those already known to affect neuronal cells can thus be identified. For example, new drugs that alleviate anxiety, analogously to Valium, which augment or stimulate the action of the important inhibitory transmitter gamma-aminobutyric acid (GABA), can be identified. Antidepressants, such as Prozac, enhance the action of serotonin, an indoleamine with a wide variety of functions. Other drugs can be readily identified using the neuroblasts according to the method of the invention. Other examples include psychoactive compounds. For example, cocaine facilitates the action of dopamine, whereas certain antipsychotics antagonize or inhibit this catecholamine. Another example is nicotine which activates the acetylcholine receptors which are distributed throughout the cerebral cortex. Therefore, by using neuroblasts derived from neuronal cells from the appropriate regions of the brain, drugs and trophic factors which bind various receptors and would produce similar effects on neuronal cells can be identified using the method of the invention.

As described above, perpetualization of a neuronal cell can be accomplished without the use of oncogenic intervention. However, if desired the neuroblast of the invention may be immortalized to maintain the cell at a defined developmental stage. The present techniques for immortalization typically involve the transfection of an oncogene to the cell, therefore, immortalization of a neuroblast can be achieved by introduction of at least one oncogene to the neuroblast. Transfection of the oncogene can be accomplished by several conventional methods well known to those skilled in the art, including using recombinant retroviruses, chemical, or physical methods. Recombinant retrovirus transfer is the preferred method of the invention for immortalization of neuroblasts. The host neuroblast can be immortalized with a particular oncogene by such methods of transfection as calcium phosphate co-precipitation, conventional mechanical procedures such as microinjection, insertion of a plasmid encased in liposomes, or by use of viral vectors. For example, one method is to use a eukaryotic viral vector, such as simian virus 40 (SV40) or bovine papilloma virus, to transiently infect or transform the neuroblast (*Eukaryotic Viral Vectors,* Cold Spring Harbor Laboratory, Gluzman ed., 1982).

Various viral vectors which can be utilized for immortalization as taught herein include adenovirus, herpes virus, vaccinia, and preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus (gag, env, and pol genes) under the control of regulatory sequences within the long terminal repeat (LTR). These plasmids are missing a nucleotide sequence which enables the packaging mechanism to recognize an RNA transcript for encapsidation. Helper cell lines which have deletions of the packaging signal include, but are not limited to Ψ2, PA317, PA12, CRIP and CRE, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Alternatively, NIH 3T3 or other tissue culture cells can be directly transfected with plasmids encoding the retroviral structural genes gag, pol and env, by conventional calcium phosphate or lipofection transfection. These cells are then transfected with the vector plasmid containing the genes of interest. The resulting cells release the retroviral vector into the culture medium.

Herpes virus-based vectors may also be used to transfer genes into a neuroblast. Since herpes viruses are capable of establishing a latent infection and an apparently non-pathogenic relationship with some neural cells, such vector based on HSV-1, for example, may be used. Similarly, it should be possible to take advantage other human and animal viruses that infect cells of the CNS efficiently, such as rabies virus, measles, and other paramyxoviruses and even the human immunodeficiency retrovirus (HIV), to develop useful delivery and expression vectors.

When a recombinant retrovirus is engineered to contain an immortalizing oncogene, the oncogene can be any one of those known to immortalize. For example, such commonly used immortalizing genes include genes of the myc family (both c-myc and v-myc) (Bartlett, et al., *Proc.Natl.Acad.Sci. USA* 85:3255, 1988), adenovirus genes (Ela 12s and Ela 13s) (Ruley, et al., *Nature* 304:602, 1983), the polyoma large T antigen and SV40 large T antigen (Frederiksen, et al., *Neuron* 1:439, 1988). Preferably, the oncogene used to immortalize the neuroblast of the invention is v-myc. Other genes, for example other nuclear oncogenes, that immortalize a cell but may require a second gene for complete transformation, will be known to those of skill in the art.

The same transfection methods described above for immortalization of a neuroblast can be utilized to transfer other exogenous genes to the neuroblast of the invention. An "exogenous gene" refers to genetic material from outside the neuroblast which is introduced into the neuroblast. An example of a desirable exogenous gene which would be useful for the method of identifying neuropharmacological compounds is a gene for a receptor molecule. For example, such neuronal receptors include the receptor which binds dopamine, GABA, adrenaline, noradrenaline, serotonin, glutamate, acetylcholine and various other neuropeptides. Transfer and expression of a particular receptor in a neuroblast of specific neural origin, would allow identification of neuroactive drugs and trophic factors which may be useful for the treatment of diseases involving that neuroblast cell type and that receptor. For example, a neuroactive compound which mimics a neurotransmitter and binds to a receptor and exhibits either an antagonistic or agonist effect, thereby inhibiting or stimulating a response in the neuroblast, can be identified using the method of the invention.

In another embodiment, the invention provides a culture system useful for the production and maintenance of a neuroblast comprising a serum-free basal media containing at least one trophic factor and a vessel having a surface which allows attachment of the neuroblast. The culture system can be utilized to produce a neuroblast from any tissue of neural origin as described above. The "serum-free basal media" of the invention refers to a solution which allows the production and maintenance of a neuroblast. The basal media is preferably a commonly used liquid tissue culture media, however, it is free of serum and supplemented with various defined components which allow the neuroblast to proliferate. Basal media useful in the culture system of the invention is any tissue culture media well known in the art, such as Dulbecco's minimal essential media, which contains appropriate amino acids, vitamins, inorganic salts, a buffering agent, and an energy source. Purified molecules, which include hormones, growth factors, transport proteins, trace elements, vitamins, and substratum-modifying factors are added to the basal media to replace biological fluids. For example, progesterone, sodium selenite, putrescine, insulin and transferrin are typically added to the basal media to enhance neuroblast growth and proliferation. For the culture system of the invention, only two of the defined supplements are necessary to sustain growth of neurons alone (transferrin and insulin), whereas the combination of the five supplements above have a highly synergistic growth-stimulating effect. Deletion of any single supplement results in markedly diminished growth of the neuroblast. An example of a preferred prototype medium which contains these elements is N2 medium (Bottenstein and Sato, et al., *Proc.Natl.Acad.Sci. USA,* 76:514, 1979). The optimal concentration of the supplements are as follows: 5 $\mu$g/ml insulin, 100 $\mu$g/ml transferrin, 20 nM progesterone, 100 $\mu$M putrescine, and 30 nM selenium (as $Na_2SeO_3$).

The basal media of the culture system further contains at least one trophic factor for the production and maintenance of a neuroblast. Most preferably, neurotrophic factors are utilized and specifically bFGF. bFGF is utilized in the basal media at a concentration from about 1 ng/ml to about 100 ng/ml, more specifically from about 5 ng/ml to about 70 ng/ml, and most preferably from about 15 ng/ml to about 60 ng/ml. Neural cultures are generally maintained at pH 7.2–7.6. A higher requirement for glucose is also necessary for neural as opposed to non-neural cells. Therefore, the basal media of the invention contains a concentration of from about 0.01% to about 1.0% glucose and preferably from about 0.1% to about 0.6% glucose.

The invention also provides a cellular composition comprising an enriched population of neuroblast cells. The composition preferably contains a majority of or at least about 90% neuroblasts. The neuroblast cells are derived from any CNS neural tissue such as from any region of the brain, as described above, or from the spinal cord. The neuroblast may be further immortalized with an oncogene, or it may contain an exogenous gene encoding a receptor or a ligand for a receptor.

The present invention also provides a method of treating a subject with a neuronal cell disorder which comprises administering to the subject a therapeutically effective amount of the neuroblast of the invention. "Therapeutically effective" as used herein, refers to that amount of neuroblast that is of sufficient quantity to ameliorate the cause of the neuronal disorder. "Ameliorate" refers to a lessening of the detrimental effect of the neuronal disorder in the patient receiving the therapy. The subject of the invention is preferably a human, however, it can be envisioned that any animal with a neuronal disorder can be treated with the neuroblast of the invention. Preferably, the neuroblast is derived from neuronal tissue of the same species as the species of the subject receiving therapy.

The method of treating a subject with a neuronal disorder entails intracerebral grafting of neuroblasts to the region of the CNS having the disorder. Where necessary, the neuroblast can be genetically engineered to contain an exogenous gene. The disorder may be from either disease or trauma (injury). Neuroblast transplantation, or "grafting" involves transplantation of cells into the central nervous system or into the ventricular cavities or subdurally onto the surface of a host brain. Such methods for grafting will be known to those skilled in the art and are described in *Neural Grafting in the Mammalian CNS,* Bjorklund and Stenevi, eds., (1985), incorporated by reference herein. Procedures include intraparenchymal transplantation, (i.e., within the host brain) achieved by injection or deposition of tissue within the host brain so as to be apposed to the brain parenchyma at the time of transplantation.

Administration of the neuroblasts of the invention into selected regions of the recipient subject's brain may be made by drilling a hole and piercing the dura to permit the needle of a microsyringe to be inserted. The neuroblasts can alternatively be injected intrathecally into the spinal cord region. The neuroblast preparation of the invention permits grafting of neuroblasts to any predetermined site in the brain or spinal cord, and allows multiple grafting simultaneously in several different sites using the same cell suspension and permits mixtures of cells from different anatomical regions. The present invention provides a method for transplanting various neural tissues, by providing previously unavailable proliferating neuroblasts and a culture system for production of these neuroblasts in order to grow a sufficient number of cells for in vitro gene transfer followed by in vivo implantation.

The neuroblast used for treatment of a neuronal disorder may optionally contain an exogenous gene, for example, an oncogene, a gene which encodes a receptor, or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by a donor neuroblast would be beneficial in a disorder where the subject's neural cell is defective in the production of such a gene product. A neuroblast genetically modified to secrete a neurotrophic factor, such as nerve growth factor, (NGF), might be used to prevent degeneration of cholinergic neurons that might otherwise die without treatment. Alternatively, neuroblasts to be grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia-nigra of the midbrain, which have the basal ganglia as their major target organ. Alternatively, neuroblasts derived from substantianigra neuronal cells which produce dopamine could be introduced into a Parkinson's patient brain to provide cells which "naturally" produce dopamine.

Other neuronal disorders that can be treated similarly by the method of the invention include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic neuroblasts, or neuroblasts containing an exogenous gene for a factor which would promote survival of these neurons can be accomplished by the method of the invention, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this invention. For example, antisense sequences, or a gene encoding an antagonist can be transferred to a neuroblast and implanted into the hippocampal region of the brain.

The method of treating a subject with a neuronal disorder also contemplates the grafting of neuroblasts in combination with other therapeutic procedures useful in the treatment of disorders of the CNS. For example, the neuroblasts can be co-administered with agents such as growth factors, gangliosides, antibiotics, neurotransmitters, neurohonnones, toxins, neurite promoting molecules and antimetabolites and precursors of these molecules such as the precursor of dopamine, L-DOPA.

The following examples are intended to illustrate but not limit the invention. While they are typical of those that might be used, other procedures known to those skilled in the art may alternatively be used.

EXAMPLES

The following examples show neuronal proliferation of hippocampal, spinal cord, substania nigra, basal forebrain, and other neuronal tissue cells from fetal rats cultured over 5 months with bFGF. In addition, adult hippocampus was cultured with bFGF in a defined media for more than 7 months. The examples also provide methodology for the generation, differentiation and long term culture of numerous cell types from fetal and adult neuronal tissue and describe the morphological, immunocytochemical, ultrastructural and molecular characteristics of proliferating non-neuronal and neuronal cell types in the adult bFGF treated cultures.

Proliferating cells that incorporated bromodeoxyuridine were immunopositive for neuron-specific enolase. Cells with polarized morphologies typical of well-differentiated neurons were immunopositive for the high molecular weight subunit of neurofilament protein (NFh), characteristic of mature neurons, the middle and low subunits of neurofilament protein and microtubule-associated protein 2 (MAP-2). Cells from adult mammalian hippocampus were capable of proliferation as well as long-term neurogenesis and neuronal differentiation in vitro. These cells may be a source of replacement cells in neuronal grafting. Further, the induction of proliferation and differentiation of these cells in vivo would be useful for replacement or augmentation of neuronal loss or degeneration.

Example 1

MATERIALS AND METHODS

Materials: DMEM:F12 medium, N2 supplement and laminin were obtained from Gibco/BRL (Bethesda, Md.); polyornithine (PORN) was obtained from Sigma (St. Louis, Mo.). Recombinant bFGF was from Syntex/Synergen Consortium (Boulder, Colo.). Bovine bFGF was purchased from R&D, Minneapolis, Minn. NeuroTag™ green was obtained from Boehringer Mannheim, Indianapolis, Ind. Cell proliferation kit containing bromodeoxyuridine (BrdU), anti-BrdU antibody and streptavidin/Texas Red was purchased from Amersham, Arlington Heights, Ind. The antibodies used to determine the phenotypes of cells in culture were obtained from the following sources and used at the indicated dilutions: polyclonal rabbit anti-neurofilament 200 (NF) (1:500; Chemicon International, Temecula, Calif.), monoclonal anti-neuron specific enolase (NSE) (1:50; DAKO, Carpenteria, Calif.), monoclonal anti-glia fibrillary acidic protein (GFAP) (1:500–1:10,000; Amersham, Arlington Heights, Ill.), monoclonal anti-vimentin (1:800; Boehringer Mannheim, Indianapolis, Ind.), monoclonal anti-OX-42 (1:5000; Serotec, Indianapolis, Ind.), polyclonal anti-galactocerebroside (Gal C) (1:5000; Advanced Immunochemical Services, Long Beach, Calif.), monoclonal anti-microtubule associated protein (MAP 2) (1:500; Sigma Immunochemicals, St. Louis, Mo.), polyclonal anti-fibronectin (1:2000; Telios, La Jolla, Calif.). Polyclonal nestin antibody (1:15,000) was from Dr. R McKay, MIT, Cambridge, Mass., and monoclonal high affinity bFGF receptor antibody (1:20) was from Dr. A. Baird, Whittier Institute, La Jolla, Calif. Polyclonal anti-GFAP (1:2000) was from Dr. L. F. Eng, Stanford University, Palo Alto, Calif.

Cell Culture. The brains of Fisher 344 rats (E16) were dissected, the meninges were removed and the hippocampi were isolated. Hippocampi were transferred to a 15 ml tissue culture tube and the volume was adjusted to 1–2 ml with phosphate-buffered saline (pH 7.4) supplemented with 0.6% glucose (PBS-G). Hippocampi were mechanically dissociated by trituration with a pasteur pipet (~20×) followed by trituration with a pasteur pipet fire-polished to significantly reduce the pipet bore (~20×). The cell suspension was pelleted by centrifugation at 1000 rpm for 5 minutes at room temperature. Cells were taken up in ~20 ml N2 medium (1:1 mixture of DMEM:F12 containing 20 nM progesterone, 30 nM sodium selenite, 100 $\mu$M putrescine, 3.9 mM glutamine, 5 $\mu$M/ml insulin, 100 $\mu$g/ml transferrin) and the cell number was quantified with a hemocytometer. Tissue culture plates were coated with polyornithine (PORN; 10 $\mu$g/ml) followed by laminin (10 $\mu$g/ml). Approximately 0.5–1.0×10⁶ cells/well were plated on PORN/laminin-coated 6 well plates in N2 medium containing 20 ng/ml bFGF (N2+bFGF) and cultured at 37° C. in 5% $CO_2$. Medium was changed every 3–4 days with fresh N2+bFGF. For passaging, cells were trypsinized (ATV trypsin, Irvine Scientific, Santa Ana, Calif.) and then taken up in N2+bFGF. Cells were pelleted by centrifugation and supernatant containing trypsin was removed. Cells were resuspended in 10 ml N2+bFGF and plated. Cells could be frozen in liquid nitrogen in N2+bFGF+10% dimethylsulfoxide (DMSO). For culturing, cells were thawed quickly at 37° C., added to 10 ml N2+bFGF, centrifuged to remove DMSO, resuspended in fresh N2+bFGF and plated as described before.

BrdU Incorporation Experiments. Primary neurons (passage 5) were grown for 3 days, whereupon the media was changed. On the following day cells were incubated with BrdU for either 1 day or 4 days. Cells were fixed, washed and then treated with a monoclonal antibody against BrdU for 1 hour. After washing, cells were reacted with biotinylated anti-mouse antibody (Vector Laboratories, Burlingame, Calif.) followed by streptavidin/Texas Red complex. Stained cultures were examined with a BioRad MRC600 confocal scanning laser microscope equipped with a krypton-argon laser using the YHS filter set (568 EX, 585 LP). Confocal fluorescent and Nomarski transmitted collected images were transferred to an Apple Macintosh Quadra 700, merged using Adobe Photoshop 2.01, and printed out on a GCC film recorder.

Neurotag™ Binding. Primary neurons (passage 5) grown in culture for 6 days were incubated with 10 $\mu$g/ml recombinant tetanus toxin C fragment conjugated to fluorescein isothiocyanate (NeuroTag™) in N2+bFGF and bovine serum albumin (0.1 mg/ml) for 2 hours. After washing the cells were examined in a BioRad confocal microscope as described for BrdU stained cells except using the BHS filter (488 EX, 515 LP).

Immunohistochemistry. Cells were passaged (passage 3; 4 days in culture after plating), grown in a 24-well plate, fixed in 4% paraformaldehyde in PBS, and then permeabilized with 0.25% Triton X-100 in Tris buffered saline. Cells were incubated overnight at 4° C. with polyclonal or monoclonal antibodies in the presence of 1% normal horse serum (for monoclonal antibody) or 10% normal goat serum (for polyclonal antibody). After washing, cells were incubated with biotin conjugated goat anti-rabbit IgG or horse anti-mouse IgG antibodies (Vector Laboratories, Burlingame, Calif.) for 1 hour at room temperature, followed by incubation for 1 hour at room temperature with a pre-formed mixture of avidin-biotinylated horseradish peroxidase complex (Vectastain Elite ABC kit). The reaction products were visualized with diaminobenzidine (DAB) histochemistry.

Transmission Electron Microscopy (TEM). Cultures (passage 3; four days after plating) grown on LabTek™ permanox slides (Ted Pella, Inc., Redding, Calif.) were fixed in 2% glutaraldehyde in 100 mM $PO_4$ at 37° C. for 2 hours and then rinsed and postfixed in 1% aqueous $OSO_4$ for 1 hour at room temperature. Cultures were then dehydrated in a graded ethanol series, infiltrated with Araldite resin and polymerized in situ. The glass slide was separated from the polymerized resin from which blocks of cultured cells were cut and glued to resin blanks. Sections were cut parallel to the culture substrate at a thickness of 70 nm. Sections collected on 300 mesh copper grids were stained with uranyl acetate and lead citrate and examined with a Phillips CM10 transmission electron microscope at 80 kV.

Scanning Electronic Microscopy (SEM). Cultures (passage 2; four days after plating) grown on LabTek™ glass slides were prepared as for TEM up through ethanolic dehydration. The plastic chambers were then removed, leaving the sealing gasket in place, and the slide was placed into a Pelco critical point dryer. Following drying, the slide was coated with gold-palladium to a thickness of 300 Å in a Technics sputter coater. The cells were examined in a Cambridge Stereoscan 360 scanning electron microscope at 10 kV.

Gene Transfer into Neurons. Approximately $1\times10^6$ producer cells were plated on PORN/laminin coated wells in a 6 well plate and grown overnight at 37° C. in 5% $CO_2$. Virus from producer cells was collected after overnight incubation in DMEM (Dulbecco's minimum essential medium) containing 5% fetal calf serum (FCS) or 5% bovine calf serum (BCS). Virus containing media was filtered through 0.45 $\mu$m filters and then mixed with polybrene (8 $\mu$g/ml) and bFGF (20 ng/ml). Media was removed from neuronal cultures and virus containing media was added to neuronal cultures and incubated overnight at 37° C. in 5% $CO_2$. After this infection period, the media was removed and replaced with N2 media containing 20 ng/ml bFGF. When the expression vector contained the neomycin resistant gene, the infected cells were selected in the presence of G418 (400 $\mu$g/ml). Cells were passaged and maintained as described above. The expression vectors and producer cells used were as follows:

1. Avian v-myc gene was expressed from MLV-LTR promoter and bacterial neomycin resistant gene was expressed from thymidine kinase (TK) promoter (Ryder, et al., *J Neurobiol.*, 21:356–375, 1989; Kaplan, et al., *J. Virol*,61:1731–1734, 1987; and Land, et al., *Mol. Cell. Biol.*, 6:1917–1925, 1986). A producer line was generated from Ψ2 cells. These cells grew in DMEM containing 10% FCS and 400 $\mu$g/ml G418. The day before the infection, the medium was changed with fresh DMEM containing 5% FCS.

2. Bacterial β-galactosidase gene was expressed from the MLV-LTR promoter. This expression vector contains a part of the gag gene and produces very high titer virus. There is no neomycin resistant gene in this vector. This vector was from Dr. Richard Mulligan, MIT, Cambridge, Mass.

A promoter line was generated from CRIP cells. These cells grow in DMEM containing 10% BCS. The day before the infection, the medium was changed with DMEM containing 5% BCS.

Example 2

GROWTH OF NEURONS IN VITRO

Figure 2A:
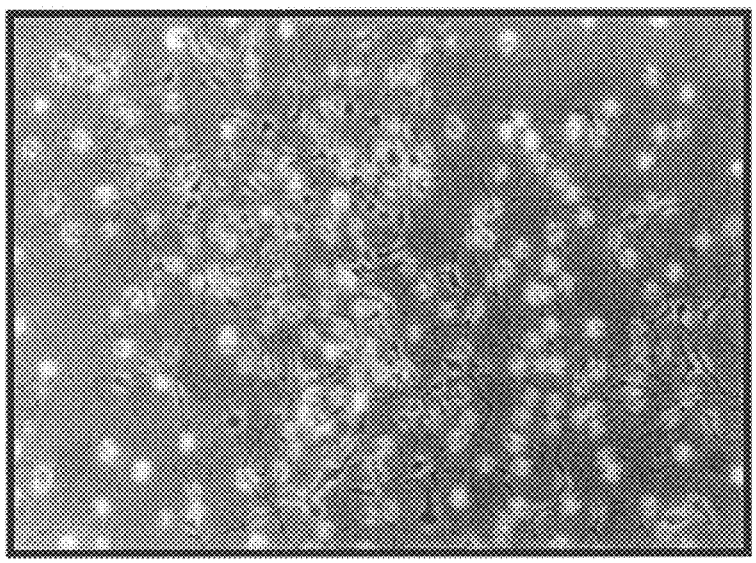
FIG. 2 illustrates photomicrographs showing the morphological changes that occur during the culture and passaging of primary neurons. A. Primary cell culture after 4 days of plating in N2+bFGF. B. Primary cells 4 days in culture after passage (passage 3). Cells were larger and interconnected by processes that also increased in size. Small proliferating cells were visible in the culture. C. Cells passaged (passage 3) and kept in culture for ~14 days in the presence of bFGF. Negative magnification 33×. D. Cells immunostained with anti-NF (200 KD) antibody, negative magnification 33×. E. Cells immunostained with anti-NSE antibody, negative magnification 33×. F. Cells immunostained with anti-GFAP antibody, negative magnification 66×.
Figure 2B:
Figure 2C:
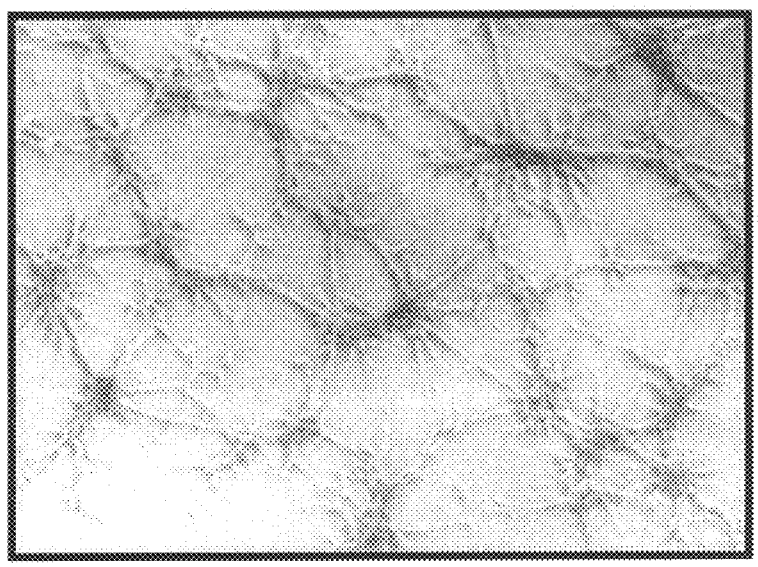

The chemically defined medium, N2 (Bottenstein and Sato, *Proc. Natl. Acad. Sci. USA*, 76: 514–517, 1980; Bottenstein, J. E., In: Cell culture in the neurosciences, J. E. Bottenstein and G. H. Sato, Eds., Plenum Press, New York, N.Y., pp 3–43, 1985; di Porizo, et al., *Nature*, 288:370–373, 1980), has been used to reproducibly generate short-term virtually pure neuronal cultures (Bottenstein, et al., *Exp. Cell Res.*, 125:183–190, 1980; Barnes and Sato, *Anal. Biochem.*, 102:255–302, 1980). This medium does not support the survival or proliferation of non-neuronal cells and it is possible to obtain >95% pure neuronal culture. In defined medium, primary cultures of hippocampal neurons die within 7 days but can be maintained for 2–4 weeks in the presence of hippocampal explants, a feeder layer of astrocytes, in astrocyte-conditioned medium (Banker, G. A., *Science*, 209:809–810, 1980) or in the presence of bFGF (Walicke and Baird, *Proc. Natl. Acad. Sci. USA*, 83:3012–3016, 1986; Walicke, P. A., *J Neurosci.*, 8:2618–2627, 1988; Walicke, et al., In: *Prog. Brain Res.*, vol. 78, D. m. Gash and J. R. Sladek, Eds. (Elsevier Science Publishers B.V.), pp 333–338, 1988). However, cells continued to die slowly and few cells remained after 1 month (Walicke, P., et al., *Proc. Natl. Acad. Sci. USA*, 83:3012–3016, 1986).

bFGF at 20 ng/ml, a concentration of about 100 fold higher concentration than that used before to study the survival and elongation of axons (Walicke, P. et al., *Proc. Natl. Acad. Sci. USA*, 83:3012–3016,1986.; Walicke, P. A., *J. Neurosci.*, 8:2618–2627, 1988), showed dramatic proliferative effects on hippocampal cells. This proliferative property of bFGF was used to promote continued proliferation of primary hippocampal cells to form a long-term culture. Cells cultured in 20 ng/ml bFGF began proliferating by 2 days, with a doubling time of 4 days. Primary cells became contact inhibited for growth and reached a plateau after day 7, although growth continued within aggregates (FIG. 2C).

To test whether division was occurring in all cells or only in a subpopulation, cultures were incubated with BrdU for 1 or 4 days and the labeled nuclei were visualized by indirect immunofluorescence using an anti-BrdU-antibody (FIG. 1 A, B).

Figure 1B:
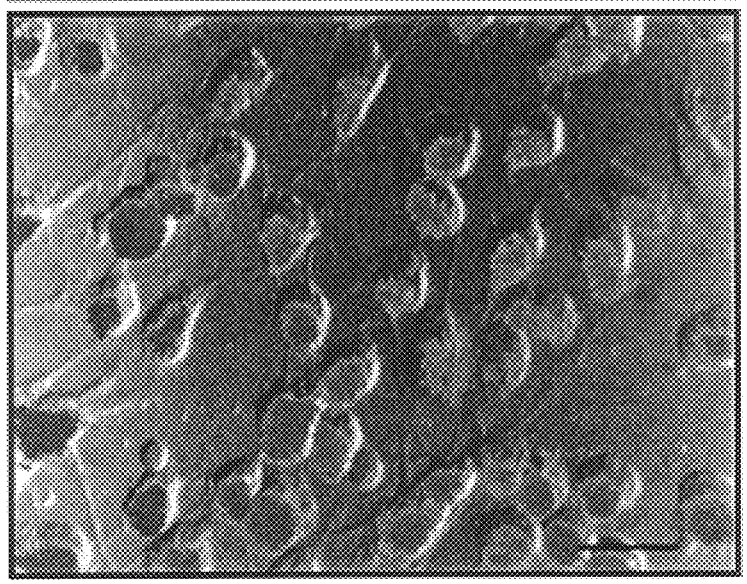
Figure 1C:
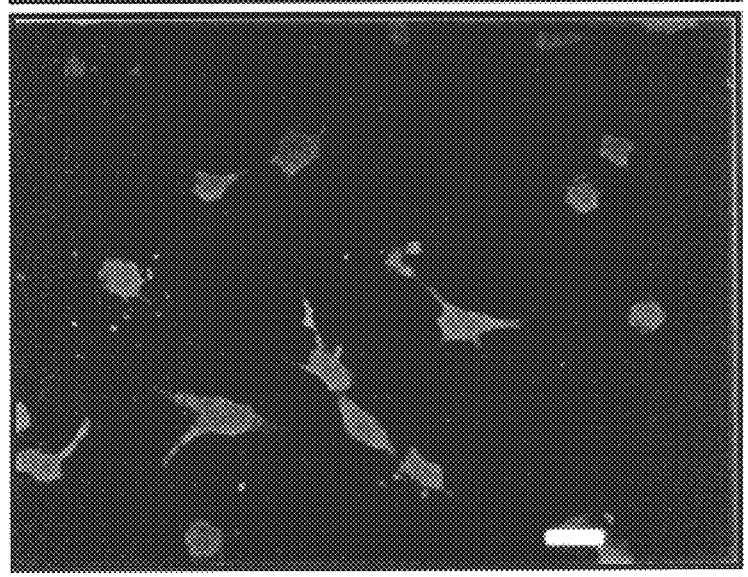

FIG. 1 shows BrdU staining and NeuroTag™ binding of primary neurons in culture. Primary neurons were labeled with BrdU for I day (A) and for 4 days (B). Only a few cells were stained on day 1, but by day 4 all cells were stained, indicating that all cells in the culture were proliferating. The neuronal nature of primary cells was determined by binding with tetanus toxin (NeuroTag™) (C). Cell bodies and processes of all cells in culture were stained. Calibration bar=20 $\mu$m. After day 1, the nuclei of only a small fraction of cells were immunostained (FIG. 1A) but almost the entire cell population was immunostained after 4 days of incubation with BrdU (FIG. 1B).

To establish long-term cultures, cells were trypsinized and passaged. The passaged cells (up to 6 passages tested) grew as well as the original culture did. Cells were frozen in liquid nitrogen, thawed and cultured again. When cells at different passage numbers were thawed and re-cultured, they grew equally well regardless of the passage number. Freeze-thawed cells showed the same morphology as the cells kept continuously in culture.

Other cells derived from neuronal tissue have also been studied for their ability to grow and be maintained in N2 media in the presence of bFGF. Table 1 shows the optimum concentrations of bFGF for culture of the various cell lines.

TABLE 1

| REGION OF CNS | CONCENTRATION OF bFGF (ng/ml)* |
|---|---|
| Hippocampus | 20 |
| Septum | 100 |
| Striatum | 20 |
| Cortex | 20 |
| Locus Coeruleus | 50 |
| Ventral Mesencephalon | 50 |
| Cerebellum | 20 |
| Spinal Cord | 20 |

*Optimum concentration of bFGF used for culture

Example 3

CHARACTERIZATION OF CELLS

Several independent criteria were used to show that the cells in the cultures were indeed neurons. These included their morphological characteristics during growth, expression of neuronal markers and ultrastructural analysis by transmission and scanning electron microscopy.

Cell morphology in culture was similar to that described for short-term cultures of neurons (Banker and Cowan, Brain Res., 126:397–425, 1977; Banker and Cowan, J. Comp. Neurol., 187:469–494, 1979) (FIG. 2A, B, C). FIG. 2 illustrates photomicrographs showing the morphological changes that occur during the culture and passaging of primary neurons. A shows primary cell culture after 4 days of plating in N2+bFGF contained numerous proliferating and process-bearing cells. B shows primary cells 4 days in culture after passage (passage 3). Cells were larger and interconnected by processes that also increased in size. Small proliferating cells were visible in the culture. C shows cells passaged (passage 3) and kept in culture for ~14 days in the presence of bFGF formed aggregates and were interconnected by an extensive network of processes forming a lattice-type pattern (Negative magnification 33×).

Cells were immunostained for several different antigenic markers. Cells were stained with anti-NF (200 KD) antibody (D); with anti-NSE antibody (E) or with anti-GFAP antibody (F). Although all cells stained with anti NF or anti-NSE antibodies, no cell staining was observed with anti-GFAP antibody. (Negative magnification 33× (D,E); 66× (F)). Cells began to proliferate by day 2 and newborn cells were small and bipolar in shape. Short processes roughly equal in length to cell bodies started to emerge from parent cells. Over the next 2–3 days, 1 or 2 of the processes started to grow rapidly and contacted the neighboring cells (FIG. 2A). By day 7, both the cell bodies and the processes had increased in size and an extensive interconnecting network of processes had formed. This morphological progression resembled hippocampal pyramidal neuronal morphologies previously described in vitro (Banker and Cowan, Brain Res., 126:397–425, 1977; Banker and Cowan, J. Comp. Neurol., 187:469–1979). When cells growing in culture for 1–2 weeks were passaged, more of these cells had processes than did the cells newly cultured from the brain (FIG. 2B). It is possible that many of these processes survived passaging, albeit partially amputated. Cells passaged and kept in culture for 14 days in the presence of bFGF formed aggregates and were interconnected by an extensive network of processes forming a lattice-type pattern (FIG. 2C). Few cells divided in open areas; most cell division occurred in the aggregates.

Figure 2D:
Figure 2E:

The cultures were characterized by immunostaining for different antigenic markers FIG. 2D, E, F; Table 1). All cell somata and their processes immunostained strongly with an antibody against NF protein which is specifically expressed by neurons (FIG. 2D). Similarly, anti-NSE antibody stained all cells in our culture (FIG. 2E; Table 1). The neuronal nature of the cells proliferating in response to bFGF was further demonstrated by the binding of tetanus toxin, a specific marker for neurons (Neale, et al., Soc. Neurosci. Abst., 14:547, 1988). NeuroTag™ green stained cell bodies and processes of all cells in the culture (FIG. 1C), indicating that the cells were neurons and that no or very few non-neuronal cells were present in the cultures. The large optical depth of field with the objective used (10×) fails to demonstrate the localization of NeuroTag™ signal as membrane bound.

Figure 2F:
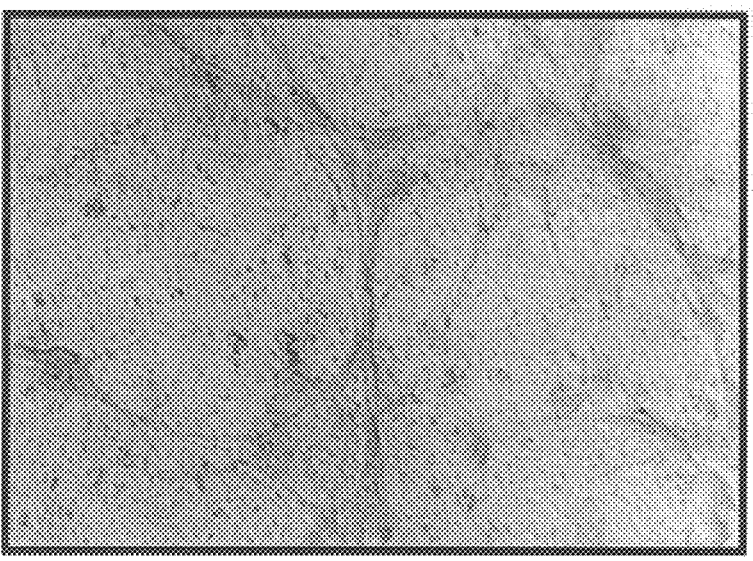

The cultures were tested by immunostaining for the presence of non-neuronal cells (Table 2). Lack of immunostaining with antibodies against GFAP indicated the absence of astrocytes (FIG. 2F). In a control experiment anti-GFAP antibody (Amersham), at the same concentration (1:10,000) immunostained rat C6 and 9L and human U373 glioma cells. The absence of oligodendrocytes and fibroblasts in our cultures was demonstrated by the lack of staining for Gal C. vimentin or fibronectin (Table 2). As a control, rat C6, 9L and human U373 glioma cells were stained with vimentin (1:800) at the same concentration as used for neuronal cultures. The results of immunostaining for other antigenic markers are shown in Table 2; these data support the conclusion that the cultures consist of neurons uncontaminated by non-neuronal cells.

TABLE 2

PROPERTIES OF PRIMARY HIPPOCAMPAL NEURONS - ANTIGENIC MARKERS FOR NEURONS AND NON-NEURONAL CELLS

| CULTURING | CHARACTERISTICS | |
|---|---|---|
| Substrate | Dependency | Yes |
| Basic FGF | Dependency | Yes |
| Freeze-Thaw | Viability | Yes |

| ANTIGENIC MARKERS | CELL SPECIFICITY | |
|---|---|---|
| Neurofilament (NF) | Neurons | ++[a] |
| GFAP | Glia | —[b] |
| Nestin | Stem cells | ++ |
| Vimentin | Glia precursors/fibroblasts | — |
| NSE | Neurons | +[c] |
| OX-42 | Microglia/macrophages | — |
| Galactocerebroside | Oligodendrocytes | — |
| MAP2 | Dendrites | + |
| Basic FGF receptor | Neurons/glia | + |
| Fibronectin | Fibroblasts | — |

++[a] cells were labeled strongly
—[b] cells were not labeled
+[c] cells were labeled weakly Example 4

ANALYSIS OF PERPETUALIZED NEURONS IN VITRO

Analysis of primary neurons in culture at the ultrastructural level demonstrated the histotypic neuronal morphology of these cells (FIGS. 3 and 4), in agreement with previous ultrastructural studies (Bartlett and Banker, J. Neurosci. 4:19440–19453, 1984; Rothman and Cowan, J. Comp. Neurol., 195:141–155, 198 1; Peacock, et al., Brain Res., 169:23 1–246, 1979). FIG. 3 shows transmission electron micrographs of primary neurons in culture. A shows a pyramidal-shaped primary hippocampal neuron showing both the soma and processes, including a major apical process (arrow) and a finer caliber process (arrowhe ad). Bar=10 $\mu$m. B shows an enlarged view of the neuronal soma shown in panel A. Bar=1 $\mu$m. C shows a portion of the major apical process of the neuron shown in panel A. This process is dominated by microtubules and polysomal ribosomes identifying it as a primary dendrite. Bar=1 $\mu$m. D shows contact between two neuritic processes. Bar=0.1 $\mu$m.

The well-differentiated neurons exhibited a histotypic pyramidal morphology, including a primary, apical dendrite with multiple ramifications, finer caliber axons, and characteristic nuclear morphology (FIGS. 3 and 4). A TEM micrograph of a pyramidal-shaped primary hippocampal neuron is shown in FIG. 3A. The level of this section encompasses both the soma and processes, including a major apical process (arrow) and a finer caliber process emerging from the basal aspect of the soma (arrowhead). Other processes from adjacent neurons are also seen. The soma of the neuron has a euchromatic nucleus with a peripheral rim of heterochromatin and a somewhat reticulated nucleolus (FIG. 3B). Mitochondria and microtubules are present in the perikaryal cytoplasm, which is dominated by rosettes of polysomal ribosomes. A portion of the major apical process of the neuron is dominated by microtubules and polysomal ribosomes identifying it as a primary dendrite (FIG. 3C). Contact between 2 neuritic processes is shown in FIG. 3D. The larger process containing a mitochondrion, microtubules and vesicles is being contacted by a swollen, bouton-like structure arising from a finer caliber process. The junction between such processes is typically vague and immature at this age in culture. Although the membranes at the site of contact appear to be uniformly parallel, there is little indication of further assembly of synaptic structures. The contents of the bouton-like process ending are unclear, appearing to be an accumulation of vesicles, with a possible coated vesicle near the site of contact.

FIG. 4 shows scanning electron micrographs of primary neurons in culture. A shows an overview of primary hippocampal neurons in culture including well-differentiated pyramidal somata (arrow) with large processes containing multiple levels of branching and less-differentiated, rounded neurons with large, extended processes (arrowheads). Bar= 50 μm. B shows a major apical dendrite emerging from a well-differentiated pyramidal neuron showing a smooth, regular caliber process just proximal to the first (major) bifurcation with several smaller processes, possibly axons emerging from it. The PORN/laminin coating the vessel surface can be seen as a porous carpeting which is absent in some patches. Bar=2 μm. C shows a well-differentiated neuron (in the middle of the field) possessing a large pyramidal soma (compare to FIG. 3A) and a large apical dendrite (arrowheads) contacted by a number of processes from other neurons. Other less-differentiated neurons which are fixed in the process of dividing were also present (arrows). Bar=20 μm. D shows an enlarged view of the dividing neuron in the upper field of view in panel C. The membrane connecting the two daughter cell components is clearly continuous, although cytokinesis is apparently underway. Note the process extension from this less-differentiated neuron, indicating some degree of differentiation during mitosis. Bar=10 μm.

Figure 3A:
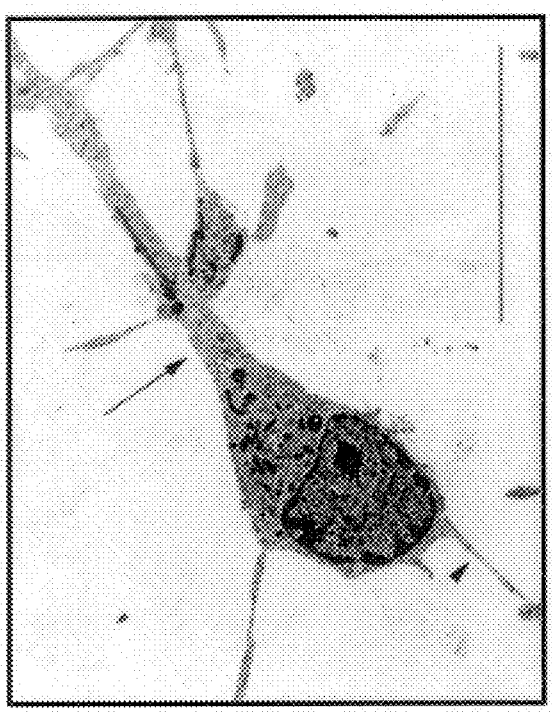
FIG. 3 shows transmission electron micrographs of primary neurons in culture. A. A pyramidal-shaped primary hippocampal neuron showing both the soma and processes, including a major apical process (arrow) and a finer caliber process (arrowhead). Bar=10 $\mu$m. B. Enlarged view of the neuronal soma shown in panel A. Bar=1 $\mu$m. C. A portion of the major apical process of the neuron shown in panel A. Bar=1 $\mu$m. D. Contact between two neuritic processes. Bar=0.1 $\mu$m.
Figure 3B:
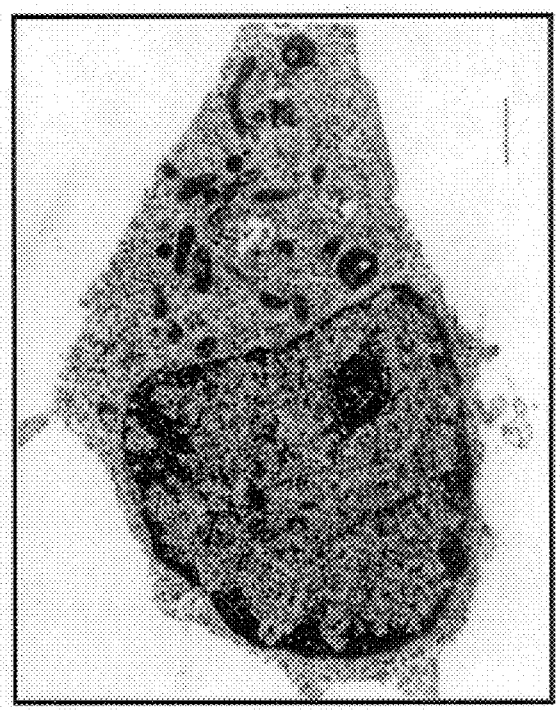
Figure 3C:
Figure 3D:
Figure 4A:
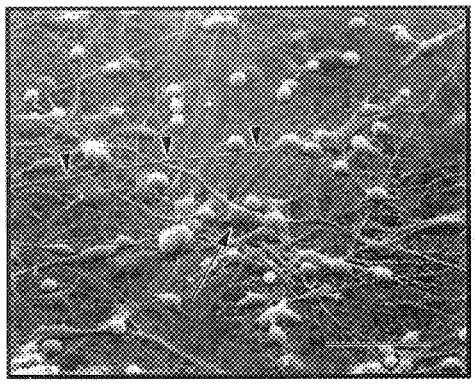
FIG. 4 shows scanning electron micrographs of primary neurons in culture. A. Overview of primary hippocampal neurons in culture including well-differentiated pyramidal somata (arrow) with large processes containing multiple levels of branching and less-differentiated, rounded neurons with large, extended processes (arrowheads). Bar=50 $\mu$m. B. A major apical dendrite emerging from a well-differentiated pyramidal neuron showing a smooth, regular caliber process just proximal to the first (major) bifurcation with several smaller processes, possibly axons emerging from it. The PORN/laminin coating the vessel surface can be seen as a porous carpeting which is absent in some patches. Bar=2 $\mu$m. C. A well-differentiated neuron (in the middle of the field) possessing a large pyramidal soma (compare to FIG. 3A) and a large apical dendrite (arrowheads) contacted by a number of processes from other neurons. Other less-differentiated neurons which are fixed in the process of dividing were also present (arrows). Bar=20 $\mu$m. D. Enlarged view of the dividing neuron in the upper field of view in panel C. Bar=10 $\mu$m.
Figure 4B:
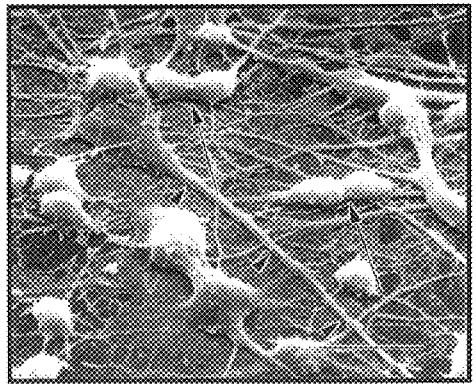
Figure 4C:
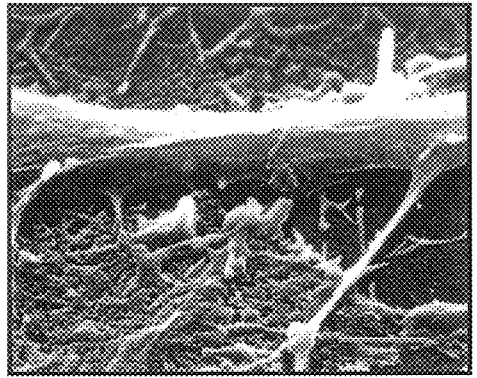

Scanning EM of primary hippocampal neurons in culture showed the diversity of morphologies present, with some well-differentiated pyramidal somata (FIG. 4A; arrow) extending large processes which show multiple levels of branching and some less-differentiated, rounded neurons. Even these rounded neurons possess large, extended processes (FIG. 4A; arrowheads). Closer examination of the major dendritic processes arising from the well differentiated neurons shows large caliber processes with acute bifurcations (FIG. 4B). A number of small caliber, axon-like processes are seen emerging from these major apical dendrites (FIG. 4B). Well-differentiated neurons typically possess a large pyramidal soma (FIG. 4C compare to FIG. 3A). When less-differentiated neurons are examined, many of these are found to have been fixed in the process of dividing (FIG. 4C; arrows). A closer view of the dividing neuron shows that, although cytokinesis is apparently underway, the membrane connecting the two daughter cell components is clearly continuous. The daughter cell component to the right is extending a fine caliber, possibly axonal, process into the foreground. Extending from this component into the upper right of the field is another thicker, dendrite-like process which undergoes several levels of branching.

Figure 4D:
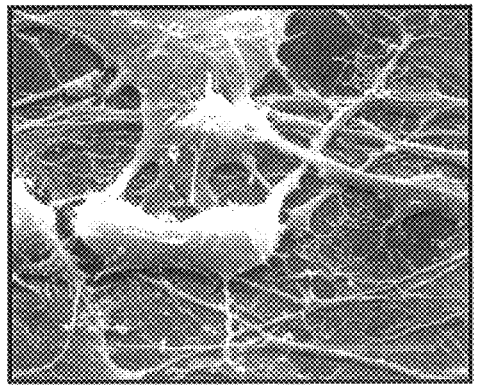

In contrast to the previous ultrastructural reports (Banker and Cowen, Brain Res., 126:397–425, 1977; Banker and Cowen, J. Comp. Neurol., 187:469–494, 1979; 29 Rothman, et al., J. Comp. Neurol., 195:141–155, 1981), the perpetualized neurons had fine caliber axonal processes which emerged from the soma in a histotypic manner in addition to the dendritic origin (FIGS. 3A and 4D). These somatic axonal extensions may be the result of the high levels of trophic support. Less-differentiated neurons typically had rounder somata with fewer, less elaborate processes. Even rounded neurons, differentiated adequately to extend processes, appeared capable of proliferating (FIG. 4D). Neuronal processes and somata have been identified based on both the ultrastructural surface morphology and organelle content, which clearly demonstrates that both the well-differentiated and proliferating, less-differentiated cells are neurons.

Example 5

EFFECTS OF DIFFERENT GROWTH FACTORS ON CELL CULTURING

Tissues were dissected from the specific areas of the central nervous system (CNS) and dissociated as described in EXAMPLE 1. After centrifugation, cells were resuspended in N2 medium and cells were counted. Approximately $0.5–1.0\times10^6$ cells were plated on PORN/laminin coated 24 well plates in N2 medium containing different growth factors at different concentrations, depending on the specific region of the CNS. Cells were cultured at 37° C. in 5% $CO_2$. Cells were examined, and if necessary, counted in 5 separate areas in a well at day 1, 4, and 7 to determine the growth rates in the presence of various growth factors (TABLE 3).

In some experiments, no proliferation of cells was observed in the presence of certain growth factors. In some cases there was massive cell death, although a small population of cells survived up to day 4. These surviving cells did not look healthy, however, addition of bFGF at 20–100 ng/ml (depending on the origin of the tissue), in N2 medium rescued these surviving cells as evidenced by this proliferation (see a, TABLE 3).

TABLE 3

EFFECTS OF DIFFERENT GROWTH FACTORS ON PROLIFERATION OF CNS NEURONS

| Region | Growth Factor | Concentration | Effect |
|---|---|---|---|
| Hippocampus | bFGF | 20 ng/ml | ++ |
|  | NGF[a] | 20 ng/ml | — |
|  | EGF | 20 ng/ml | + |
|  | BDNF | 20 ng/ml | — |
|  | NT3 | ND* | + |
| Septum | bFGF | 100 ng/ml | ++ |
|  | NGF[a] | 100 ng/ml | — |
|  | EGF[a] | 100 ng/ml | — |
|  | BDNF[a] | 100 ng/ml | — |
|  | NT3[a] | ND* | — |
| Locus Ceruleus | bFGF | 50 ng/ml | ++ |
|  | NT3 | ND* | — |
| Ventral Mecencephalon | bFGF | 50 ng/ml | ++ |
|  | BDNF | 50 ng/ml | — |
|  | EGF | 50 ng/ml | — |
| Cerebellum | bFGF | 20 ng/ml | ++ |
|  | EGF | 20 ng/ml | + |
|  | NGF | 20 ng/ml | — |
|  | BDNF | 50 ng/ml | — |
|  | NT3 | 50 ng/ml | — |
| Spinal Cord | bFGF | 20 ng/ml | ++ |
|  | NT3 | 20 ng/ml | + |

TABLE 3-continued

EFFECTS OF DIFFERENT GROWTH FACTORS
ON PROLIFERATION OF CNS NEURONS

| Region | Growth Factor | Concentration | Effect |
| --- | --- | --- | --- |

*conditioned medium from genetically modified fibroblasts expressing NT3 was used; ND - not determined
++ high proliferation
— no proliferation
+ moderate proliferation
[a] cells could be rescued and proliferated by bFGF Example 6

PREPARATION OF ADULT NEURONAL CULTURES

Hippocampi of normal adult Fisher rats were dissociated and grown in serum-free culture containing bFGF as described in Example 1. Briefly, hippocampi were dissected from normal adult (>3 mo) rat brains. Most of the choroid plexus, ependymal lining and sub-ependymal zone was removed. Cells were dissociated mechanically and enzymatically using methods described previously (Ray, et al., 1993, supra) with the following modifications: After enzymatic dissociation in a papain-protease-DNase (PPD) solution (Hanks balanced salt solution supplemented with 4 mM $MgSO_4$ and 0.01% papain, 0.1% neutral protease and 0.01% DNaseI), cells were centrifuged at 1000 g for 3 min, resuspended and triturated in 1 ml of DMEM:F12 (1;1) high glucose medium (Ivine Scientific)+10% fetal bovine serum (10% FBS) (Sigma). Cells were plated onto uncoated plastic T-75 culture flasks (Costar) at $1 \times 10^6$ viable cells per flask in 10% FBS medium overnight. Lower cell densities were used with smaller culture flasks or Lab-Tek slide chambers (Nunc). Cells were occasionally plated onto cultureware previously coated with polyornithine/laminin as described in Example 1. The medium was removed the next morning and replaced with serum-free medium: DMEM:F 12+N2 (GIBCO) at 1 ml/100 ml medium (N2), +bFGF (recombinant human bFGF, Syntex/Synergen Consortium; (Ray, et al., supra) at 20 ng/ml. Flasks were incubated 1–3 weeks, when half of the medium was removed and replaced with the same volume of fresh N2+bFGF. Partial medium exchange was made 1–2 × weekly or as needed. Cultures were examined and photographed using phase contrast microscopy (Nikon Diaphot).

In a number of experiments cells were harvested and transferred directly to new flasks or Lab-Tek slide chambers where they attached immediately and started proliferating, or occasionally passaged using trypsinization with ATV trypsin (Irvine Scientific), followed by washing, centrifugation and re-plating in N2+bFGF.

Primary cultures of neurons from adult rat hippocampi were replicated more than 15 times. To determine whether 10% FBS or N2 medium could account for the observed effects, some cultures were grown in 10% FBS or N2. Only cultures with bFGF developed large numbers of neurons. Some dissections were made of the CA1, CA3 and dentate gyrus regions. Neurons were generated from all three regions. Cultures are described in three overlapping temporal stages: early, middle and late.

Early cultures (1–21 days) were characterized by cell attachment to the substrate, cell proliferation and expression of mature neuronal features. After clearing cell debris in the medium, single cells that were phase-bright and round and doublet cells, suggestive of cell division, were observed at two days in vitro (d.i.v.). Numerous phase-bright cell bodies displayed processes tipped with growth cones. Cells of neuronal morphologies, i.e., phase-bright multipolar cell body with thin branching processes, were observed as early as 5 d.i.v.. Processes developing complex branching patterns and evidence of incomplete cytokinesis or potential synapse formation between presumptive sibling neurons were observed as early as 8 d.i.v.. (Nikon phase contrast-2 microscope/negative magnification 33×–66×).

For SEM, cultures were fixed in 2% glutaraldehyde in 0.1 M PBS, osmicated in 1% aqueous osmium tetroxide, dehydrated in a graded ethanol series, critical point dried with liquid carbon dioxide, attached to stubs with silver paste, sputter coated to 300 Å with gold/palladium and examined and photographed in a Cambridge Scanning Electron Microscope (Stereoscan 360).

Examination of the three-dimensional morphology of early /intermediate stage cultures using scanning electron microscopy (SEM) revealed numerous cells of both neuronal and epithelioid phenotypes. Lacy neural networks were observed as with phase microscopy. Cells that appeared to be dividing were also observed. Higher magnification revealed that the processes between cells and cell aggregates interpreted at the light microscope level as a single process were frequently 2 or more fasciculated processes.

Intermediate cultures (approximately 14–60 days) were characterized by increasing numbers of cells, the presence of neural networks, the development of mature neurons and initial cell aggregate formation. Rudimentary networks of fine processes connecting small cell clusters were observed as early as 14 d.i.v. Networks of cells displaying neuronal morphologies became more extensive and complex. Cells in the cultures were heterogeneous although individual patches of neural networks displayed a uniform morphological phenotype. Individual cells away from clusters or networks also developed well differentiated morphological features characteristic of mature neurons, with large phase-bright multipolar cell bodies and long thin processes that branched repeatedly. Processes of these cells often measured nearly 1000 um, and large indented nuclei and prominent nucleoli could be seen in different focal planes. Some neurons displayed small thom-like projections indistinguishable from dendritic spines on processes.

Late cultures (approximately 2 to 7 months) were characterized by increasing numbers of cells to confluence, increasing cell aggregates connected by processes and a background of individual cells. When substrate space was available, cells with multiple thin processes characteristic of earlier stages continued to be observed. Cell aggregates were connected by cable-like neurites. Large numbers of cell aggregates developed and the entire substrate became covered with cell aggregates and individual cells that appeared to have migrated from the cell aggregates. While many background cells displayed features typical of neurons, some cells expressed features typical of astrocytic glia.

Example 7

GENE EXPRESSION IN CULTURED NEURONAL CELLS

The presence of NFh and GFAP was further confirmed by reverse transcriptase-polymerase chain reaction (RT-PCR) with RNA obtained from cells harvested after different times in culture.

RNA was extracted using the guanidinium—cesium chloride (CsCl) method (Current Protocols in Molecular Biology, Vol. 1, Wiley Interscience, NY, F. M. Ausubel, et al., eds, 1988). The pellets were solubilized in 1 ml solution D (4.0M guinidine thiocyanate, 25 mM Na citrate, 0.5% sarcosyl and DEPC treated $H_2O$) after thawing, triturated gently and the cell lysate was transferred to CsCl previously poured into centrifuge tubes. The level of the CsCl was marked, and the tubes were weighed and balanced. The tubes were centrifuged in a Beckman Ultracentrifuge overnight at 40,000 rpm at 20° C. The next morning, solution D was removed, and the interface washed with solution D. The CsCl solution was carefully poured off, and the RNA pellet was rinsed with 70% EtOH (made with DEPC water). After the pellet was dry it was solubilized in DEPC-$H_2O$ and the remainder was stored in EtOH at −70° C.

A RT-PCR method was used to obtain cDNA's (Ausubel, et al., 1988, supra). The reaction tube contained 4 μl RNA (10–100 ng). 8 μl (sufficient DEPC-$H_2O$ to bring the volume up to 20 μl), 2 μl 10 X PCR buffer, 2 μl 10 mM d NTP's, 1 μl random hexamers, 3 μl 24 mM MgCl, 0.125 μl AMV-RT and 0.5 μl RNasin. A drop of Nujol mineral oil was added to each tube and the reaction was run in a Perkin Elmer Thermal Cycler: 42° C.—75 min; 95° C.—10 min; and held at 4 ° C.

A PCR method was used to further amplify the specific desired cDNAs from the cDNAs obtained above. Each reaction tube contained 5 μl cDNA, 9.5 μl PCR buffer, 7.25 μl $MgCl_2$, 0.2 or 0.3 μl $^{32}$P-dCTP, 1.5 μl 10 mM dNTP's, 0.5 Taq polymerase, 6 μ, 1 primers (2 μl [1 μl (F (Forward rx):5')+1 μl R (reverse:3') each of RPL 27, NFh, GFAP, NGF or bFGF) and sufficient $H_2O$ to bring the volume to 100 μl. The reaction was run in a Perkin Elmer Thermal Cycler: 94° C.—10 min and held at 4° C.

AmpliTaq DNA polymerase was from Perkin-Elmer, AMV reverse transcriptase, random oligonucleotide hexamer primers and recombinant RNasin ribonuclease inhibitor were from Promega, specific primers were made to order. dNTP's were from New England Nuclear. The primers were as follows:

NFh

Forward (F) primer: 5'-GAGGAGATAACTGAGTACCG-3'

Reverse (R) primer: 5'-CCAAAGCCAATCCGACACTC-3'

GFAP

F primer: 5'-ACCTCGGCACCCTGAGGCAG-3'

R primer: 5'-CCAGCGACTCAACCTTCCTC-3'

Gel electrophoresis of cDNA-samples obtained from PCR amplification was done on a 6% non-denaturing polyacrylamide gel. Some samples and their corresponding digests were run on agarose gels using ethidium bromide to bind and illuminate the DNA under UV light. A 123 bp molecular ladder was run in a lane beside the samples. Electrophoresis was done for varying periods of time, and the resulting gels were dried for 1 hr on a gel drier. Autoradiographic films of dried acrlyamide gels were developed for periods of time ranging from several hours to 10 days.

Relative levels of MRNA were analyzed quantitatively using densitometry over cDNA bands identified as NFh, GFAP, NGF and bFGF from Northern blots of cultures grown 36 to 117 days. A diverging pattern of MRNA expression was apparent. Expression of message for NFh was relatively low. At about 2 months, the relative levels switched and expression of mRNA for GFAP increased over time then dropped dramatically at about 4 months in culture, while expression of NFh fell over time, then rose slightly after 4 months in culture.

Digests of NFh were performed on samples remaining from earlier reactions using a cocktail consisting of 40 μl sample, 5 μl React #6 buffer (50 mM Tris, pH 7.4, 6 mm $MgCl_2$, 50 mM KCl, 50 mM NaCl) and 5 μl Pvu II restriction enzyme, and reacted for 1 hr at 37° C. The products were run along with a 123 bp molecular ladder on a 6% acrylamide gel. The gel was dried, exposed on film for varying periods of time, and the resulting autoradiograms were examined for bands at the predicted molecular weight levels. mRNA for both NFh and GFAP was present in all cultures at the times examined.

Example 8

IMMUNOCYTOCHEMISTRY

To determine whether cells expressed antigens typical of neural tissue, cultures were processed for immunocytochemistry. Cells were fixed for 30 min in 4% paraformaldehyde at room temperature or 37° C., incubated with 0.6% $H_2O_2$ in TBS followed by incubation in blocking solution. The cultures were incubated with primary antibody at appropriate dilutions overnight at 4° C. The next day cells were rinsed with diluent and incubated in secondary antibody for 1 hr at room temperature, rinsed with TBS and incubated in ABC solution (equal amounts of avidin and biotin) for 1 hr at room temperature. They were rinsed with TBS and incubated with DAB-NiCl for variable reaction times, rinsed with TBS, dried overnight, dehydrated through graded series of alcohol and mounted in histoclear. Antibodies were from the following sources and used at the dilutions indicated. Monoclonal antibodies: high molecular weight sub-unit of neurofilament protein (NF-H 200 kD; 1:24); middle molecular weight sub-unit of neurofilament protein (NF-M 160: 1:10); glial filament acidic protein (GFAP; 1:100) and synaptophysin (1:10) (Boelringer Mannheim); calbindin (Cal-b; 1:200) and microtubule associated protein 2 (MAP2; 1:500) (Sigma); neuron-specific enolase (NSE;1:200) (DAKO). Polyclonal antibodies: NF-H 200 (1:250); NF-M 150 (1:500); NF-L 68 (1:125); GFAP (1:1000) and gamma amino butyric acid (GABA; 1:200) (Chemicon); NSE (1:800) (Polysciences); galactocerebrocide (Gal-C; 1:5000) (Advanced Immuno Chem.); bFGF (1:1000); (Whittier Institute, La Jolla, Calif.). Normal horse and goat serum, biotinylated goat anti-rabbit IgG, horse anti-mouse IgG and ABC Vectastain Elite kit were from Vector Laboratories (Burlingame, Calif.). There was no detectable staining when primary antibody was omitted and replaced with non-immune serum.

Neuro-specific enolase (NSE)-positive cells were observed in early cultures. By 170 d.i.v., a majority of the cells were immunoreactive for high molecular weight neurofilament protein (NFh, 200 kD) that is characteristic for adult neurons, as well as the middle and low molecular weight of NF. Most NF-positive cells also had morphological properties of neurons. A small subpopulation of cells (less than 10%) was immunopositive for calbindin, which is specific for granule cells. Cells with neuronal phenotypes were also immunopositive for MAP2 with reaction product localized to the cytoplasm of cell bodies and proximal processes. Cells with astroglial morphology stained for GFAP. Less than 1% of the cells stained for GABA. Many cells were immunopositive for bFGF and a few small round cells were immunopositive for galactocerebroside.

Example 9

CHARACTERIZATION OF NEURONAL CELL GROWTH IN VITRO

To determine whether cells were proliferating and, if so, assess the nature of such cell types, cultures were incubated in bromodeoxytiridine (BrdU) for 36 hours and then dual labeled for immunofluorescence with BrdU and neuron-specific enolase (NSE) or glial filament acidic protein (GFAP).

For BrdU incorporation, cells were cultured in glass Lab-Tek slide chambers for 11 days. The medium was replaced with fresh N2+bFGF containing bromodeoxyuridine (BrdU) labeling reagent (1 μl/ml medium; Amersham) and the cultures were incubated an additional 1 or 4 days for a total of 12 or 15 days. Cells were fixed in 4% paraformaldehyde in phosphate-buffered saline (PBS) for 30 min, washed with PBS, blocked with 10% normal donkey serum (Jackson ImmunoResearch Labs) in PBS, and reacted with monoclonal antibody to BrdU (BrdU; undiluted; Amersham) followed by donkey anti-mouse IgG coupled to Cy-5 (Jackson immunoResearch Labs). Some cultures were dual labeled with polyclonal antibody against neuron specific enolase (NSE; 1:800) or antibody against glial fibriliary acidic protein (GFAP; 1:1000). Secondary antibody for the polyclonals was donkey anti-rabbit IgG conjugated to fluorescein isothiocyanate (FITCH Jackson ImmunoResearch Labs). Slides were mounted in Slow-Fade mounting reagent (Molecular Probes). Cells were visualized using a BioRad MRC 600 Confocal Scanning Laser Microscope. Images were collected and transferred to an Apple MacIntosh Quadra 700, merged using Adobe Photoshop 2.01 and printed out on a GCC film recorder.

Confocal scanning microscopy revealed cells immunoreactive for NSE and BrdU, as well as BrdU and GFAP positive cells showing that cells expressing neuronal and glial cell markers dividing in these cultures.

To determine if cell numbers in culture were increasing, cells were counted over a 2 week period in 10 random fields. Thirty-seven percent of cells originally attached had survived by the second day in culture. Within 5 days, cell numbers had risen to slightly above their original level, and by the end of seven days, there were nearly twice as many cells. By the end of 2 weeks, there were almost five times as many cells as on the first day in culture.

The most important result of this study is the demonstration of neuronal proliferation from normal adult hippocampus when cultured with bFGF. Neurons survive and proliferate abundantly for long periods of time, more than 200 d.i.v. to date; this is the first such demonstration.

It has been reported that initiation of cell division of isolated adult brain (striatal) cells in culture requires epidermal growth factor (EGF), but not bFGF at 20 ng/ml, and a non-adhesive substrate (Reynolds & Weiss, Science, 755:1707, 1992). In contrast, the present data supports that: 1) bFGF at 20 ng/ml acts as a strong mitogen and as a survival factor in adult as well as fetal hippocampal cultures; 2) proliferation occurs in substrate-bound cells and aggregates, i.e., cells not in suspension, and 3) many, if not most, of the cells that attach are bFGF-responsive.

Limited neuronal division as been reported over short times in other culture systems of adult brain (Reynolds, supra; Richards, et al. *Proc. Natl. Acad. Sci., USA*, 89:8591, 1992). In the present study proliferation was confirmed by BrdU incorporation and the finding that cell numbers increased almost 500% over a 2 week period. Although it has been reported that less that 1% of adult striatal cells initially plated proliferate (Reynolds, et al. supra), in the cultures described herein nearly 40% of cells which initially attached survived to the second day in culture, suggesting that many cells are present in adult hippocampus that have the capacity to proliferate.

Evidence from several independent experiments supports the idea that most cells in these cultures not only are neurons, but they are mature neurons which express morphological, biochemical and molecular features characteristic of adult neurons. While glia are also generated, glia were a minority phenotype in most cultures. Similar findings have been reported for fetal rat hippocampus neurons cultured with bFGF (Ray, et al., 1993, supra).

The source of the proliferating neurons for the adult brain remains to be determined. The cells could be mature functioning neurons that were saved and induced to proliferated by high concentration of bFGF; the cells could be stem cells of suspected proliferation zones; or the cells could be partially committed neurons (neuroblasts) that have become quiescent due to a reduction in high levels of bFGF present only in the embryonic brain and/or because of contact inhibition. While it is unlikely that all neurons that were observed and generated could be accounted for the mature neurons saved following plating, work is in progress to determine whether mature differentiated neurons are capable of in vitro survival and proliferation through dedifferentiation. It is possible that the subventricular zone (SVZ) could be the source of these cells, since SVZ of mammalian forebrain has been shown to be the source of these cells that differentiate into neurons and glia in adult mice (Clois, et al., *Proc. Nat'l Acad. Sci. U.S.A.*, 79:2074, 1993). However, it is not likely that the SVZ could have served as the main source of proliferating cells in the cultures of the invention, since the ependyimal lining/SVZ, along with choroid plexus, was stripped away. These neurons could be derived from a small population of embryonic stem cells that survives in the adult brain in a dormant, non-proliferative state, as has been suggested exists in adult mouse striatum (Reynolds, et al., supra). Alternatively, these neurons could be neuronal precursor cells existing in adult mammalian brain that require discrete epigenetic signals for their proliferation and differentiation as has been speculated for adult mouse brain (Richards, et al., supra).

In addition to stem cells of the SVZ, there is a large population of neuroblast in the normal adult mammalian hippocarnpus that can be induced to generate large numbers of neurons over long periods of time under appropriate in vitro conditions. It is possible that this could also be true in vivo, a concept that has profound implications for basic and clinical neuroscience. This could mean that normal hippocampus and, by extension, normal CNS has a reservoir of cells that can be activated under appropriate conditions to replicate large numbers of neurons. Thus, neuroblasts could be present not only in cultures of fetal CNS, but also in cultures of adult CNS and in the adult CNS in situ.

Example 10

LONG-TERM CULTURE OF NEURONS FROM ADULT HIPPOCAMPUS

Brains of adult Fisher rats (>3 months old) were dissected, the menengies removed, and the hippocampai dissected out. The tissues were transferred to a 15 ml tissue culture tube and washed three times with 5 ml Dulbecco's phosphate buffered saline (D-PBS). After the last wash, the tissue was pelleted by centrifugation at 1000 g for 3 min and the wash solution removed. The tissue was suspended in 5 ml papain-neutral protease-DNase (PPD) solution and incubated at 37° C. for 20–30 min with occasional shaking. The solution was made in Hank's balanced salt solution supplemented with 12.4 mM $MgSO_4$ containing 0.01% papain, 0.1% neutral protease and 0.01% DNase I (London, R. M. and Robbins, R. J., *Method. Enzymol.*, 124:412–424, 1986).

Hippocampai were mechanically dissociated by tituration with a medium bore pasteur pipet (about 20 times). Cells were pelleted by centrifugation at 1000 g for 3 min. The cells were resuspended in I ml DMEM:F12 (1:1) medium containing 10% fetal bovine serum, 3.9 mM glutamine (complete medium). Cell clumps were mechanically dissociated by tituration with medium to fine bore pasteur pipets (about 20 times with each). Cells were washed with 5–10 ml complete medium twice by centrifugation. Cells were taken up in 1 ml complete medium, dissociated by tituration and counted in a hemocytometer. Cells were plated at a density of $1 \times 10^6$ cells/T75 flasks (Coaster) and incubated at 37° C. in 5% $CO_2$/95% air incubator. After incubation for 18–24 hours, the medium was changed with N2 medium [1:1 mixture of DMEM/F-12 containing 20 nM progesterone, 30 nM sodium selenite, 100 $\mu$M putrescine, 3.9 mM glutamine, insulin (5 $\mu$g/ml) and transferrin (100 $\mu$g/ml)] containing 20 ng/ml FGF-2 (bFGF). To date cells have been cultured for at least 7 months and have been cultured from 15 different independent dissections.

The neuronal nature of cells were determined by examination of morphology at light and scanning microscope levels. Immunocytochemical analysis showed that these cells expressed neuron-specific enolase, neurofilament medium and high molecular weight proteins, MAP-2, and calbindin (only a small population). Some cells in these cultures also stained for GFAP indicating the presence of astrocytes in these cultures. The proliferation of adult neuronal cells in cultures was determined by bromodeoxyuridine (BrdU) incorporation. The nuclei of cells expressing neuron-specific enolase were immunostained with an antibody against BrdU indicating cell proliferation in culture.

Example 11

IN VIVO SURVIVAL OF PERPETUAL HIPPOCAMPAL NEURONS AFTER GRAFTING IN THE ADULT BRAIN

Embryonic hippocampal neurons were cultured in N2 medium containing 20 ng/ml bFGF. Cells were passaged and allowed to grow until 70–80% confluent. The medium was replaced with fresh medium (N2+bFGF) containing $^3$H-thymidine (1 $\mu$Ci/ml; specific activity: 25 Ci/mmol) and allowed to grow for 3.5 days. Cells were harvested from flasks by trypsinization and washed with D-PBS 3 times by centrifugation. Cells were resuspended in 2 mls of D-PBS containing 20 ng/ml bFGF, dissociated by tituration and counted in a hemocytometer. After centrifugation to remove the supernatant, cells were resuspended at a concentration of 60,000 cells/$\mu$l. One microliter of cell suspension was injected in the hippocampus of adult Fisher rats (>3 months old). Animals were perfused with 4% paraformaldehyde, and the brains removed. Brain sections were treated with antibodies with calbindin, GFAP and NF-H proteins. The sections were dipped in emulsion and developed after 6 weeks. Number of cells with at least 12 grains on them were counted in every 12 sections for each animal (3 animal total). At three weeks, an average of 17% cells implanted in the brain survived (Table 4).

TABLE 4

SURVIVAL OF PERPETUAL HIPPOCAMPAL NEURONS IN ADULT RAT HIPPOCAMPUS

| ANIMAL | AVERAGE # CELLS WITH GRAINS/SECTION | % CELLS SURVIVING |
|---|---|---|
| 1 | 222 | 15 |
| 2 | 233 | 19 |
| 3 | 244 | 17 |

Although the invention has been described with reference to the presently preferred embodiment, it should be understood that various modifications can be made without departing from the spirit of the invention.

We claim:

1. A culture system used for the production and maintenance of a neuroblast comprising:
   (a) a serum-free basal media containing at least one trophic factor selected from the group consisting of bFGF. EGF and NT3, wherein the trophic factor is present at a concentration of between about 1 ng/ml to 100 ng/ml: and
   (b) a tissue culture vessel, wherein a surface of the tissue culture vessel allows attachment of the neuroblast.

2. The culture system of claim 1, used for the production and Maintentance of a neuroblast, further comprising a neuroblast derived from neural tissue selected from the group consisting of hippocampus, cerebellum, spinal cord, cortex, striatum, basal forebrain, ventral mesencephalon, and locus ceruleus.

3. The culture system of claim 1, wherein the trophic factor is basic fibroblast growth factor.

4. The culture system of claim 1, wherein the trophic factor is present at a concentration of from about 5 ng/ml to about 70 ng/ml.

5. The culture system of claim 1, wherein the trophic factor is present at a concentration from about 15 ng/ml to about 60 ng/ml.

6. The culture system of claim 3, wherein the glucose is present at a concentration from about 0.01% to about 1.5%.

7. The culture system of claim 3, wherein the glucose is present at a concentration from about 0.1% to about 0.6%.

8. The culture system of claim 1, wherein the surface in the vessel is treated with a polybasic amino acid.

9. The culture system of claim 8, wherein the polybasic amino acid is polyornithine.

10. The culture system of claim 1, wherein the surface in the vessel is treated with an extracellular matrix molecule.

11. The culture system of claim 10, wherein the extracellular matrix molecule is selected from the group consisting of laminin, collagen, and fibronectin.

12. The culture system of claim 1, wherein the serum-free basal media further comprises glucose.

13. The culture system of claim 2, wherein the neuroblast is a mammalian neuroblast.

14. The culture system of claim 13, wherein the neuroblast is selected from the group consisting of a human, a mouse and a rat neuroblast.

* * * * *